US011298078B2

(12) United States Patent
Oehler et al.

(10) Patent No.: US 11,298,078 B2
(45) Date of Patent: Apr. 12, 2022

(54) CAPACITIVE TEXTILE ELECTRODE, METHOD FOR PRODUCING IT, AND USE

(71) Applicant: CAPICAL GMBH, Braunschweig (DE)

(72) Inventors: Martin Oehler, Braunschweig (DE); Heiko Gronostay, Braunschweig (DE); Henning Boege, Braunschweig (DE)

(73) Assignee: Capical Gmbh, Braunschweig (DE)

( * ) Notice: Subject to any disclaimer, the term of this patent is extended or adjusted under 35 U.S.C. 154(b) by 1150 days.

(21) Appl. No.: 14/911,122

(22) PCT Filed: Aug. 12, 2014

(86) PCT No.: PCT/EP2014/067249
§ 371 (c)(1),
(2) Date: Feb. 9, 2016

(87) PCT Pub. No.: WO2015/022327
PCT Pub. Date: Feb. 19, 2015

(65) Prior Publication Data
US 2016/0192881 A1      Jul. 7, 2016

(30) Foreign Application Priority Data
Aug. 14, 2013   (DE) .................. 10 2013 108 810.4

(51) Int. Cl.
*A61B 5/00*      (2006.01)
*A61B 5/25*      (2021.01)

(52) U.S. Cl.
CPC .............. *A61B 5/6804* (2013.01); *A61B 5/25* (2021.01); *A61B 2562/0214* (2013.01);
(Continued)

(58) Field of Classification Search
CPC ................ A61B 5/0408; A61B 5/6804; A61B 2562/0214; A61B 2562/125;
(Continued)

(56) References Cited

U.S. PATENT DOCUMENTS 5,010,772 A *  4/1991  Bourland ............... A61B 5/113
                                                    73/172
2008/0045808 A1*  2/2008  Hassonjee .............. D02G 3/441
                                                    600/300
(Continued)

FOREIGN PATENT DOCUMENTS

DE   20 2006 007 226 U1   10/2007
DE   10 2006 038 362 A1    2/2008
(Continued)

OTHER PUBLICATIONS

DE-102008049112-A1 (Daimler AG) Translated by Espacenet May 7, 2009 [Retrieved on Apr. 4, 2019].*
(Continued)

*Primary Examiner* — Eun Hwa Kim
*Assistant Examiner* — Adam Z Minchella
(74) *Attorney, Agent, or Firm* — WCF IP

(57) ABSTRACT

The invention relates to a capacitive textile electrode for capacitively measuring electric signals, in particular biological signals, wherein the electrode has a multilayer structure which has at least two electrically conductive layers which are composed of a textile material and has at least one insulation layer which is arranged between the at least two electrically conductive layers, characterized by one, several or all of the following features: a) the at least two electrically conductive layers are mechanically connected to one another and/or to the insulation layer by adhesive bonding, b) at least one several or all of the electrically conductive layers have a prefabricated electrically conductive textile sheet material and/or a prefabricated textile EMC shielding material or comprise the same, c) at least one, several or all of the electrically conductive layers are in the form of textile pieces which have been cut by laser beam, d) at least one amplifier electronics system for amplifying the electrical signals emitted by the capacitive electrode is integrated into
(Continued)

Figure 1:
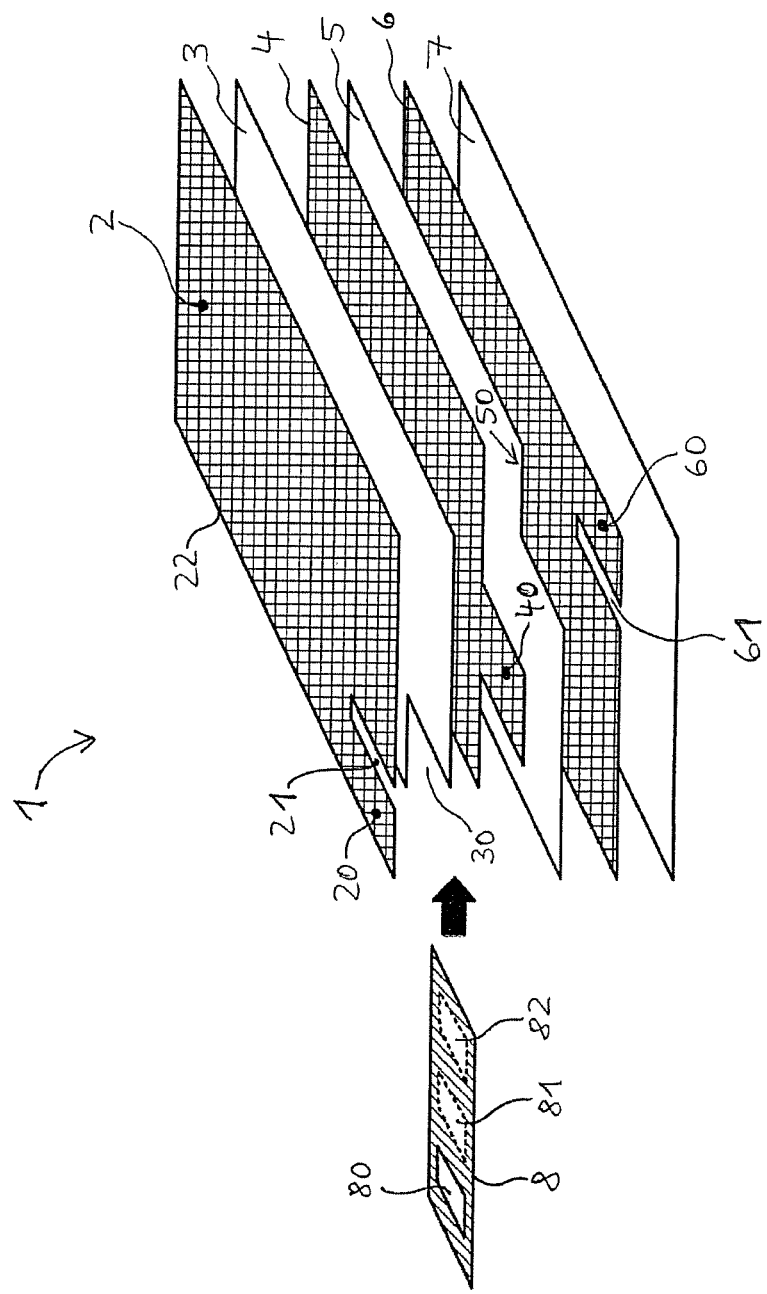

the multilayer structure of the capacitive electrode. The invention further relates to the use of prefabricated electrically conductive textile sheet material and/or prefabricated textile EMC shielding material for producing a capacitive textile electrode, and to a method for producing a capacitive textile electrode.

11 Claims, 4 Drawing Sheets

(52) U.S. Cl.
CPC ... *A61B 2562/125* (2013.01); *A61B 2562/182* (2013.01); *A61B 2562/227* (2013.01)

(58) Field of Classification Search
CPC ........ A61B 2562/227; A61B 2562/182; A61B 18/1442; A61B 18/1402; A61B 2018/1405; A61B 2018/1412; A61B 2018/1427; A61B 2018/1462; A61B 2018/1495; A61B 2018/146; A61B 18/1445; A61B 2018/1455
See application file for complete search history.

(56) References Cited

U.S. PATENT DOCUMENTS

| | | | |
|---|---|---|---|
| 2013/0345539 A1* | 12/2013 | Quintanar | A61B 5/6822 600/385 |
| 2015/0276430 A1* | 10/2015 | Sekitani | G06F 3/0445 324/609 |

FOREIGN PATENT DOCUMENTS

| | | | | |
|---|---|---|---|---|
| DE | 10 2008 025 525 A1 | | 12/2008 | |
| DE | 10 2008 049112 A1 | | 5/2009 | |
| DE | 102008049112 A1 | * | 5/2009 | ........... A61B 5/6893 |
| DE | 102010023369 A1 | * | 12/2010 | ............. B60N 2/002 |
| WO | 2008/148713 A2 | | 5/2008 | |
| WO | 2013/050621 A2 | | 10/2012 | |
| WO | 2012/149466 A2 | | 11/2012 | |
| WO | WO-2012149466 A2 | * | 11/2012 | ........... A61B 5/6833 |

OTHER PUBLICATIONS

DE-102008049112-AI (Daimler AG); Translated by Espacenet May 7, 2009 [Retrieved on Apr. 4, 2019] (Year: 2009).*
DE-102010023369-AI (Daimler AG); Translated by Espacenet Dec. 30, 2010 [Retrieved on Aug. 31, 2020] (Year: 2010).*

* cited by examiner

CAPACITIVE TEXTILE ELECTRODE, METHOD FOR PRODUCING IT, AND USE

The invention relates to a capacitive textile electrode for the capacitive measurement of electrical signals, in particular of biosignals, according to the preamble of claim 1. The invention also relates to the use of prefabricated electrically conductive textile sheeting and/or prefabricated textile EMC shielding material for the production of a capacitive textile electrode according to claim 9 and also to a method for producing a capacitive textile electrode according to claim 10.

Generally, the invention relates to the field of capacitive electrodes for the capacitive measurement of electrical signals. By means of the capacitive detection principle, electrical signals can be detected without direct galvanic contacting by using a detectable body. Such capacitive electrodes are suitable for example for the detection of biosignals on living beings, for example for the detection of ECG signals or heart rate signals.

A proposal for a capacitive textile electrode is already disclosed by DE 10 2008 049 112 A1.

Against this background, the object of the present invention is to provide a capacitive textile electrode that can be produced more easily and efficiently and is consequently particularly suitable for mass production. Furthermore, an advantageous production method for such an electrode and also an advantageous use of prefabricated electrically conductive textile sheeting and/or prefabricated textile EMC shielding material is to be provided.

This object is achieved according to claim 1 by a capacitive textile electrode for the capacitive measurement of electrical signals, in particular of biosignals, wherein the electrode has a multilayer structure, which comprises at least two electrically conductive layers of a textile material and at least one insulating layer arranged between the at least two electrically conductive layers, characterized by one or more or all of the following features:
  a) the at least two electrically conductive layers are mechanically connected to one another and/or to the insulating layer by adhesive bonding,
  b) at least one or more or all of the electrically conductive layers comprise(s) or consist(s) of a prefabricated electrically conductive textile sheeting and/or a prefabricated textile EMC shielding material,
  c) at least one or more or all of the electrically conductive layers are formed as textile pieces trimmed by a laser beam,
  d) at least one amplifier electronics system for amplifying the electrical signals emitted by the capacitive electrode is integrated in the multilayer structure of the capacitive electrode.

The invention has the advantage that the capacitive textile electrode mentioned can be produced in an automated manner particularly efficiently with customary industrial production machines. Necessary manual activities are eliminated or reduced to a minimum. In the case of previous proposals, for example, for the production of an electrode area, i.e. an electrically conductive layer of a textile material, it was necessary to weave or stitch a conductive yarn into the textile material. As a difference from this, it is proposed according to one aspect of the present invention to form at least one or more or all of the electrically conductive layers at least partially from prefabricated electrically conductive textile sheeting and/or prefabricated textile EMC shielding material.

This has great technical production-related advantages. Electrically conductive textile sheeting is obtainable by the meter. The electrically conductive textile sheeting may in particular be formed as textile EMC shielding material. The abbreviation EMC stands for electromagnetic compatibility. EMC shielding materials are otherwise used for example for shielding spaces in buildings from electromagnetic radiation. EMC shielding materials in textile form, or electrically conductive textile sheetings in general, are obtainable on the market as finished products, for example from the company Statex or from the company Aaronia, for example the shielding fleece X-Dream. Such products are obtainable by the meter as roll stock and can accordingly be easily processed in an automated manner.

In the case of previous proposals, it was necessary to mechanically join together the individual layers of the multilayer structure of the electrode by sewing. Such sewing operations involve a comparatively great expenditure of time, even if automatic sewing machines or sewing robots are used. Moreover, such a production process is not as stable as desired on account of delicate thread guides. There may be downtimes and maintenance times. As a difference from this, it is proposed according to one aspect of the present invention to mechanically connect the at least two electrically conductive layers to one another and/or to the insulating layer by adhesive bonding. This can likewise be automated very efficiently. The adhesive bonding is then characterized on the basis of the adhesive used.

In the case of known electrodes, there was also the problem of providing suitable textile pieces, for example for the electrically conductive layers. Manual cutting to size is relatively unprofitable for mass production. The use of cutting robots, for example in the form of cutting plotters, does not always lead to the desired cutting quality at the edges of the pieces cut out, which can fray. Moreover, depending on the textile material used, the cutters used are subject to relatively great wear, so that time and costs for the maintenance of such systems in turn make production less profitable. Some of the textile materials used are also poor in terms of allowing themselves to be mechanically cut. As a difference from this, it is proposed according to one aspect of the present invention to form at least one or more or all of the electrically conductive layers as textile pieces trimmed by a laser beam. Consequently, a laser beam can be used to cut out the textile pieces directly from the raw material, for example the prefabricated electrically conductive textile sheeting and/or the prefabricated textile EMC shielding material. The laser cutting, for example by means of a computer-controlled laser-beam cutting device, allows the textile pieces to be quickly provided in the desired form, while the form can also be cut irregularly in any way desired. Moreover, the textile pieces provided can be further processed better and do not fray as readily.

According to a further aspect of the present invention, at least one amplifier electronics system for amplifying the electrical signals emitted by the capacitive electrode is integrated in the multilayer structure of the capacitive electrode. This has the advantage that the electrical variables provided by the capacitive electrode or by its electrically conductive layers can be electrically further processed directly in situ and can in particular be thereby amplified. This benefits the signal quality. With an amplifier electronics system arranged further away, there would be the risk of interference entering the supply leads. This can be avoided in the case of the electrode according to the invention. It is possible to provide a compact capacitive electrode, which provides at its outer electrical terminals electrical signals that have already been preprocessed by the amplifier electronics system, and which consequently can be connected directly to further-processing electrical devices. The amplifier electronics system may have any desired gain factor suitable for the respective application. The gain factor may be less than or greater than 1 or else equal to 1.

Generally, the capacitive textile electrode has the advantage that it can altogether be formed flexibly. This allows installation in everyday articles such as seats, couches or clothing. In these cases, such a flexible electrode can at least partly take up the movements occurring and deform with them. Electrodes incorporated in such articles can for example record ECGs (electrocardiographs) directly on a person sitting on a seat or lying on a couch.

The amplifier electronics system integrated in the capacitive textile electrode may likewise be formed as a flexible amplifier electronics system, for example by using a flexible printed circuit board. A non-flexible amplifier electronics system may also be used. In this case it is advantageous to keep it relatively small in terms of its surface area, in order not to impair too much the flexibility of the other areas of the capacitive textile electrode.

The textile material should be understood as meaning in particular any sheet-like textile formation, irrespective of the way in which the individual textile threads are interlinked, such as for example woven, knitted or crocheted, interwoven, laid or sewn-knitted fabrics, nonwovens and felts.

According to an advantageous development of the invention, the adhesive for the mechanical connection of the layers is an electrically conductive adhesive, which at the same time also establishes an electrical connection between at least one electrically conductive layer of the electrode and at least one electrical component connected thereto, for example the amplifier electronics system or an electrical connection cable. This has the advantage that no further electrical contacting measures are required. The step of adhesively bonding the individual layers to one another can also already establish the necessary electrical contacts. As a result, the mass production of the capacitive electrodes can be further optimized significantly. In the case of known proposals, on the other hand, contacting is required, for example by means of soldered or crimped connections or by using conductive yarn, which greatly increases the expenditure involved in production. Moreover, the electrical contacting by means of conductive adhesive allows the capacitive textile electrode to be of a more robust form. Soldered or crimped connections can no longer be damaged and break during the operation of the electrode, for example as a result of deformation of the flexible electrode. An example of an adhesive that can be used is CW 2400 from the company CircuitWorks. A two-pack adhesive with a metal component, for example a silver component, may also be used.

According to an advantageous development of the invention, the electrode has at least three electrically conductive layers of a textile material and also insulating layers arranged between the electrically conductive layers. Of the at least three electrically conductive layers, there may in particular be at least one sensor layer for the capacitive coupling of the signal to be measured by means of the electrode, at least one guard layer for shielding the sensor layer from external interfering influences and at least one reference potential layer. The reference potential layer is connected or can be connected to a reference potential, for example to a frame potential of an electrical circuit or to ground potential. The structure with the at least three electrically conductive layers mentioned has the advantage that the electrode according to the invention is particularly sensitive to the electrical signals to be detected, without being oversensitive to interference signals.

Apart from the two insulating layers arranged between the three electrically conductive layers, there may also be a third insulating layer, so that altogether a six-layer structure is obtained. The third insulating layer may be used to insulate the electrode from the surroundings, i.e. the third insulating layer is an insulating layer lying on the outside. The third insulating layer may in particular be applied on the reference potential layer.

According to an advantageous development of the invention, the guard layer is arranged between the sensor layer and the reference potential layer. As a result, the electrode is particularly insensitive to interference.

According to an advantageous development of the invention, the at least two or at least three electrically conductive layers have at least one sensor layer for the capacitive incoupling of the signal to be measured by means of the electrode, wherein the sensor layer is formed as an outer layer of the multilayer structure of the electrode that is not provided with an insulating layer on its outer side. As a result, the structure of the electrode according to the invention can be further optimized, both with regard to being easy to produce at low cost and also with regard to its function. Although in principle insulation is required on the outer side of the sensor layer for the function of a capacitive electrode, in typical cases where capacitive textile electrodes are used this insulation can be provided by the surroundings of the application, such as for example a seat covering or the surface of a clothing fabric. Accordingly, the electrode according to the invention can be further simplified with regard to its structure and its production in comparison with known proposals.

According to an advantageous development of the invention, one insulating layer has at least one clearance, which overlaps with an electrically conductive layer of textile material and through which the electrically conductive layer is in electrical contact with an electrical component. This advantageously allows a multilayer structure of the electrode without outer contact leads. The contacting may likewise be integrated in the electrode. The electrical component may be for example the already mentioned amplifier electronics system or some other component or a terminal lead. The contacting mentioned, through a clearance in the insulating layer, may be realized in the case of one or more or all of the insulating layers of the electrode.

The insulating layers may in principle be produced from any desired insulating material. It is advantageous to produce the insulating layers from flexible material, so that an altogether flexible capacitive textile electrode is created. According to an advantageous development of the invention, one or more or all of the insulating layers comprise(s) or consist(s) of an insulating textile material. This has the advantage that the insulating layers can be provided by the same processing steps as the electrically conductive layers, in particular by using a laser to cut to size prefabricated textile material that is for example provided on a roll or in some other form.

The object mentioned at the beginning is also achieved according to claim 9 by use of prefabricated electrically conductive textile sheeting and/or prefabricated textile EMC shielding material for the production of a capacitive textile electrode for the measurement of electrical signals, in particular of biosignals. In particular, an electrode of the type described above can be produced in this way. The advantages mentioned at the beginning can also be achieved thereby.

The object mentioned at the beginning is also achieved according to claim 10 by a method for producing a capacitive textile electrode for the measurement of electrical signals, in particular of biosignals, with the steps of:
a) providing a prefabricated electrically conductive textile material and also a prefabricated insulating material,
b) cutting to size the electrically conductive textile material and the insulating material into pieces of a predetermined size and form,
c) adhesively bonding the cut-to-size pieces to one another to form an electrode that has a multilayer structure which comprises at least two electrically conductive layers of the textile material and at least one insulating layer arranged between the at least two electrically conductive layers.

The mentioned steps a) to c) are advantageously carried out in the sequence indicated. As a result, a capacitive textile electrode can be produced, as described above, with the advantages likewise already described.

The cutting to size of the electrically conductive textile material and/or the insulating material into pieces of a predetermined size and form may take place by means of a laser. Then the insulating layers are formed from the insulating material and the electrically conductive layers of the electrode are formed from the electrically conductive textile material. The insulating material may in particular be an insulating textile material. The adhesive bonding of the cut-to-size pieces may take place at least partially by means of an electrically conductive adhesive. Optionally, sewing together of some or all of the layers of the electrode is additionally possible. Altogether, at least three electrically conductive layers of a textile material may be provided, between which insulating layers are respectively arranged. The at least three electrically conductive layers may be formed as described above for the electrode.

According to an advantageous development of the invention, in step c) of claim 10 an amplifier electronics system for amplifying the electrical signals emitted by the capacitive electrode is integrated in the multilayer structure of the capacitive electrode.

Figure 2:
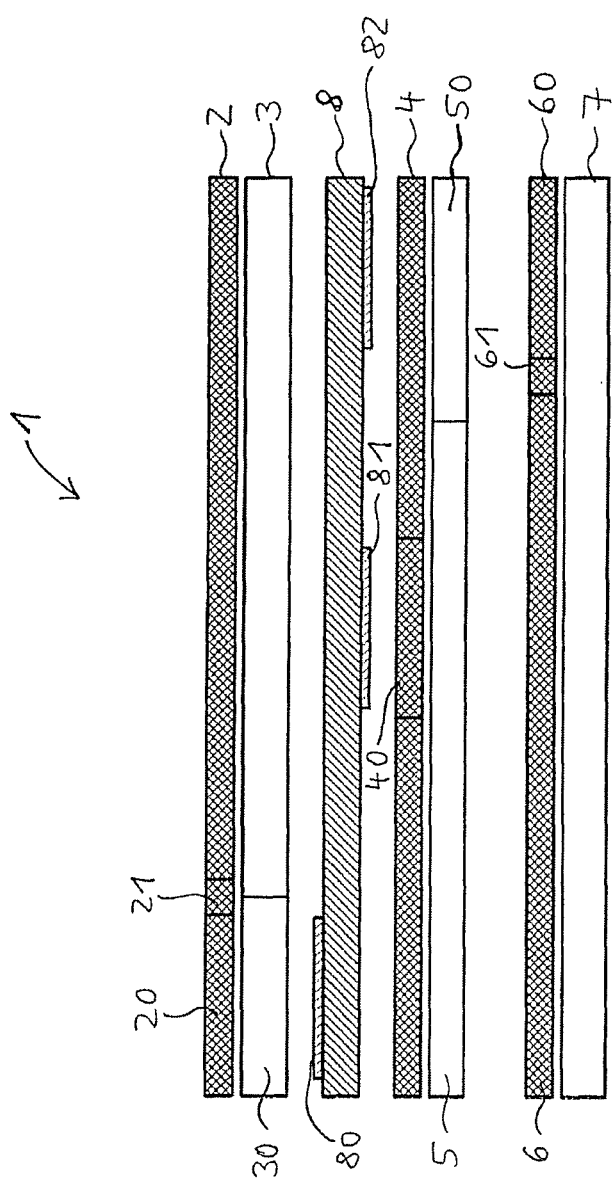
Figure 3:
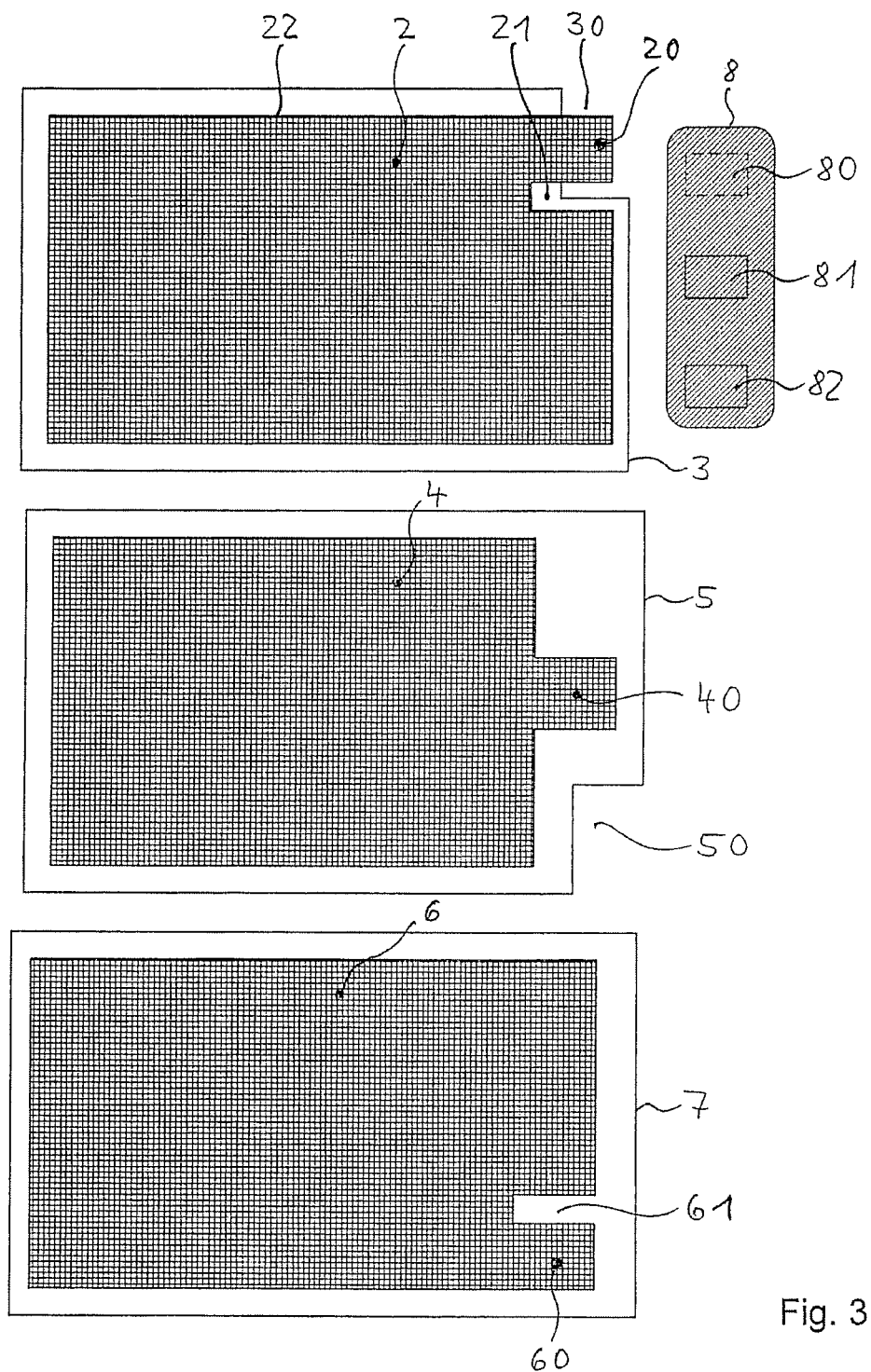
Figure 4:
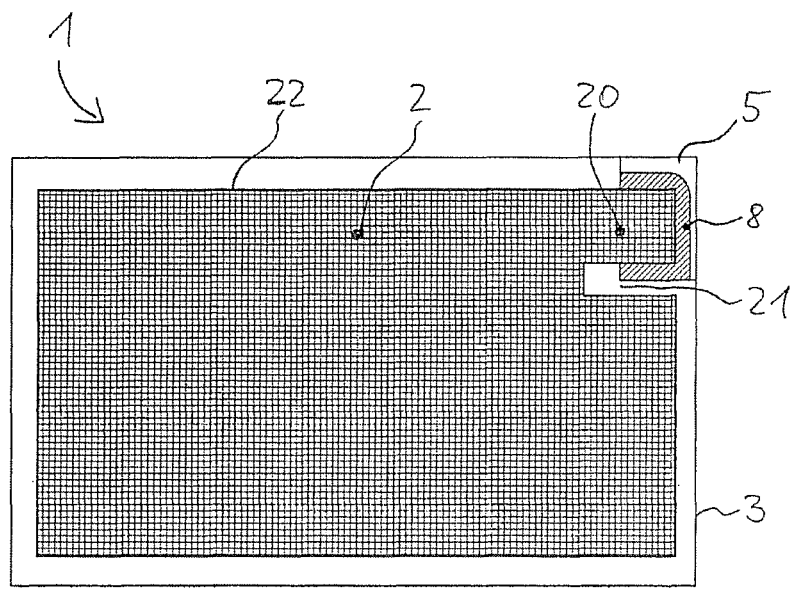
Figure 5:
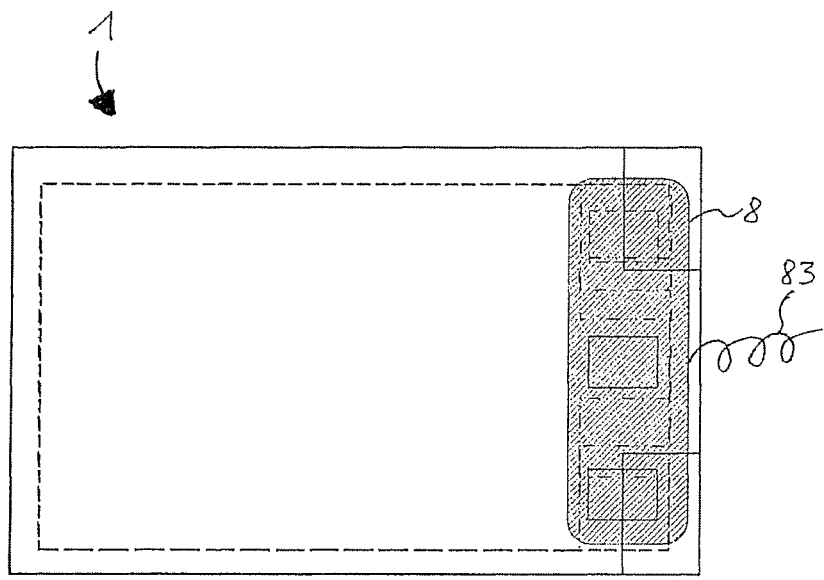

The invention is explained in more detail below on the basis of exemplary embodiments while using drawings, in which:

FIG. 1 shows an electrode in an isometric representation in the manner of an exploded drawing and FIG. 2 shows the electrode according to FIG. 1 in a lateral view and FIG. 3 shows the individual layers of the electrode according to FIG. 1 in a plan view and FIG. 4 shows the electrode according to FIG. 1 in a plan view and FIG. 5 shows the electrode according to FIG. 1 in plan view in a kind of x-ray representation.

In the figures, the same designations are used for elements that correspond to one another.

FIG. 1 shows the electrode 1 with the individual layers in an isometric view before the layers are adhesively bonded together. Three electrically conductive layers 2, 4, 6 of an electrically conductive textile material and three insulating layers 3, 5, 7 of an insulating textile material can be seen. The uppermost electrically conductive layer 2 is the sensor layer of the electrode, which serves for the capacitive incoupling of the signal to be measured by means of the electrode. The middle electrically conductive layer 4 is a guard layer, which serves for shielding the sensor layer 2 from external interfering influences, in particular ESD influences. The lower electrically conductive layer 6 is a reference potential layer, which is to be connected to a reference potential. The sensor layer 2 has at a corner a clearance 21, through which a contact link 20 for the electrical contacting of the sensor layer 2 is formed. The guard layer 4 has a contact link 40, which is formed by pieces of textile material of the guard layer 4 to the left and right of the contact link 40 having been cut away. The contact link 40 serves for the electrical contacting of the guard layer 4. The reference potential layer 6 is formed in a way comparable to the sensor layer 2, but with a contact link 60 on the opposite side. The contact link 60 is formed as the result of a clearance 61, which is cut out from the textile material of the reference potential layer 6. The uppermost insulating layer 3 has at a corner a clearance 30, which lies underneath the contact link 20. The middle insulating layer 5 has at an opposite corner of the same side a clearance 50. The clearance 50 overlaps with the contact link 60. The lowermost insulating layer 7 does not have such clearances. The layers 2, 3, 4, 5, 6, 7 may be brought into the outer contour described and shown for example by laser cutting. The outer contours are traced with a laser, whereby the clearances mentioned can also be easily created. This produces a laser-beam trimming of the textile pieces, as represented by way of example in the form of a trimming 22 of the sensor layer 2.

The outer form of the electrode 1 or the individual layers 2, 3, 4, 5, 6, 7 does not necessarily have to be substantially rectangular, as represented in FIG. 1, but may assume any other desired form, such as for example oval, rectangular with rounded corners or circular.

In the multilayer structure represented in FIG. 1, an amplifier electronics system 8, which serves for amplifying the electrical signals emitted by the capacitive electrode 1, is integrated in the region in which the contact links 20, 40, 60 are present. The amplifier electronics system 8 is in this case arranged between the upper insulating layer 3 and the guard layer 4. However, this is only one example of a possible arrangement; other positionings of the amplifier electronics system 8 are advantageously possible. The amplifier electronics system 8 has on the side represented on top in FIG. 1 an electrical terminal area 80, and on the lower side two further electrical terminal areas 81, 82, for example in the form of contact pads. As a result of the clearances 30, 50, the contact link 20 can be electrically connected to the terminal area 80, the contact link 40 to the terminal area 81 and the contact link 60 to the terminal area 82. As a result of the insulating layers 3, 5, 7 overlapping in the other regions, unwanted short-circuits or faulty contacts cannot occur.

FIG. 2 shows the electrode 1 according to FIG. 1 in a side view looking toward the narrow side of the electrode 1 on which the amplifier electronics system 8 is inserted. The terminal areas 80, 81, 82 arranged on different sides of the amplifier electronics system 8 and also the possibility of bringing them into electrical contact with the contact links 20, 40, 60 through the insulating layers 3, 5 can be seen.

FIG. 3 shows the individual layers 2, 3, 4, 5, 6 and also the amplifier electronics system 8 once again partially next to one another in a plan view, an electrically conductive layer 2, 4, 6 being respectively shown above the insulating layer 3, 5, 7 assigned to it and lying thereunder.

FIG. 4 shows the elements represented in FIG. 3 after they have been assembled to form the electrode 1, i.e. after the individual layers have been adhesively bonded to one another by using an electrically conductive adhesive. FIG. 5 shows the electrode 1 according to FIG. 4 in a kind of x-ray representation, in which deeper layers are also made visible. In particular, contours of the also amplifier electronics system 8, the terminal areas 80, 81, 82 and also the various contact links 20, 40, 60 and clearances 30, 50 can be seen.

FIG. 5 also shows by way of example the electrical contacting of the electrode 1 by means of an electrical terminal lead 83. By means of the electrical terminal lead 83, the electrical signals emitted by the amplifier electronics system 8 can be fed to a useful application, for example an ECG or heart rate detection system.

The described electrode is suitable for integration in seats, in particular chairs or vehicle seats, in couches, for example for patient monitoring, and also for integration in clothing. Important application areas of the electrode are ECG and heart rate measurement.

As can be seen, the production of the electrode according to the invention can be greatly optimized for automated production. For example, the following steps may be carried out:

- processing of electrically conductive and insulating textile material by the meter,
- cutting to size of the textiles by laser, for example from a supply roll or from cut-to-size pieces of the textile material,
- carrying out the cutting to size in such a form that later adhesive bonding and insulation or electrical contacting is already facilitated by the design of the cut-to-size piece,
- adhesive bonding of the individual textile layers to one another, for example by pressing the multilayer structure,
- use of electrically conductive adhesive for simultaneous electrical contacting,
- adhesive bonding of an amplifier electronics system into the multilayer structure,
- possibly optional sewing together of the layers.

The invention claimed is:

1. A capacitive textile electrode, comprising:
   a multilayer structure which comprises at least two electrically conductive layers of a textile sheet material and at least one insulating layer arranged between the at least two electrically conductive layers, wherein said multilayer structure is arranged for a capacitive measurement of electrical biosignals;
   at least one amplifier electronics system for amplifying electrical signals emitted by the capacitive electrode, wherein the amplifier electronics system is integrated in the multilayer structure at a position between respective ones of the at least two electrically conductive layers and comprises at least two connection areas,
   wherein at least one or more or all of the at least two electrically conductive layers
   a) comprises a prefabricated textile electromagnetic compatibility (EMC) shielding material, and/or
   b) is laser beam cut-to-size,
   wherein the at least one insulating layer comprises at least one clearance,
   wherein each of the at least two electrically conductive layers comprises a contact link which is cut out of the textile material of the electrically conductive layers, and
   wherein at least one of the contact links overlaps with the at least one clearance and is electrically and directly connected with one of the at least two connection areas through the at least one clearance.

2. The capacitive textile electrode as claimed in claim 1, wherein the at least two electrically conductive layers are mechanically connected to one another and/or to the at least one insulating layer by adhesive bonding, and wherein the adhesive for the mechanical connection of the at least two electrically conductive layers and/or the at least one insulating layer is an electrically conductive adhesive which establishes an electrical connection between at least one electrically conductive layer of the at least two electrically conductive layers and at least one electrical component connected thereto.

3. The capacitive textile electrode as claimed in claim 1 wherein said at least two electrically conductive layers includes at least three electrically conductive layers of textile sheet material, and wherein the at least one insulating layer includes at least a plurality of insulating layers, wherein the insulating layers are arranged between the at least three electrically conductive layers.

4. The capacitive textile electrode as claimed in claim 3, wherein the at least three electrically conductive layers include
   at least one sensor layer for capacitive coupling of an electrical signal to be measured
   at least one guard layer for shielding the sensor layer from external interfering influences; and
   at least one reference potential layer which is connected or connectable to a reference potential.

5. The capacitive textile electrode as claimed in claim 4, wherein the at least one guard layer is arranged between the sensor layer and the reference potential layer.

6. The capacitive textile electrode as claimed in claim 1 wherein the at least two electrically conductive layers comprise a sensor layer for capacitive coupling of the electrical biosignal to be measured, wherein the sensor layer is formed as an outer layer of the multilayer structure of the capacitive electrode that is not provided with an insulating layer on its outer side.

7. The capacitive textile electrode as claimed in claim 1 wherein the at least one insulating layer comprises an insulating textile material.

8. A method for producing a capacitive textile electrode as claimed in claim 1, comprising the steps of:
   a) providing a prefabricated electrically conductive textile material and a prefabricated insulating material,
   b) cutting to size the electrically conductive textile material and the insulating material into cut-to-size pieces of a predetermined size and form,
   c) adhesively bonding the cut-to-size pieces to one another to form the multilayer structure which comprises the at least two electrically conductive layers of the textile material and the at least one insulating layer arranged between the at least two electrically conductive layers,
   d) integrating the amplifier electronics system for amplifying electrical signals emitted by the capacitive electrode in the multilayer structure of the capacitive electrode at the position between the respective ones of the at least two electrically conductive layers, wherein the contact link of each of the at least two electrically conductive layers is cut out of the electrically conductive textile material, wherein the at least one of the contact links overlaps with the at least one clearance and is electrically connected through the at least one clearance with the one of at least two connection areas in the amplifier electronics system.

9. The method as claimed in claim 8, wherein the step of adhesively bonding of the cut-to-size pieces to one another takes place at least partially by an electrically conductive adhesive.

10. A method of measuring electrical biosignals, comprising:
- contacting or placing in close proximity with a living person or animal a capacitive textile electrode as recited in claim 1; and
- acquiring electrical biosignals from said living person or animal with said capacitive textile electrode.

11. A capacitive textile electrode, comprising:
- a multilayer structure which comprises at least two electrically conductive layers of a textile sheet material and at least one insulating layer arranged between the at least two electrically conductive layers, wherein said multilayer structure is arranged for a capacitive measurement of electrical biosignals;
- at least one amplifier electronics system for amplifying electrical signals emitted by the capacitive electrode, wherein the amplifier electronics system is integrated in the multilayer structure at a position between respective ones of the at least two electrically conductive layers and comprises at least two connection areas,
- wherein the at least one insulating layer comprises at least one clearance,
- wherein each of the at least two electrically conductive layers comprises a contact link which is cut out of the textile material of the electrically conductive layers, and
- wherein at least one of the contact links overlaps with the at least one clearance and is electrically and directly connected with one of the at least two connection areas through the at least one clearance.

* * * * *